(12) United States Patent
Guidi et al.

(10) Patent No.: US 8,512,209 B2
(45) Date of Patent: Aug. 20, 2013

(54) DEVICE FOR ANALYZING AND MONITORING EXERCISE DONE BY A USER

(75) Inventors: Jarno Guidi, Cesena (IT); Mario Fedriga, Forli' (IT); Timothy Sean O'Connell, Jr., Gambettola (IT)

(73) Assignee: Technogym S.p.A., Gambettola (IT)

( * ) Notice: Subject to any disclaimer, the term of this patent is extended or adjusted under 35 U.S.C. 154(b) by 29 days.

(21) Appl. No.: 12/253,746

(22) Filed: Oct. 17, 2008

(65) Prior Publication Data

US 2009/0105047 A1    Apr. 23, 2009

(30) Foreign Application Priority Data

Oct. 19, 2007    (IT) .............................. BO2007A0701

(51) Int. Cl.
*A63B 15/02*    (2006.01)
*A63B 71/00*    (2006.01)

(52) U.S. Cl.
USPC .................................. 482/8; 482/1

(58) Field of Classification Search
USPC ..................................... 482/1, 8–9
See application file for complete search history.

(56) References Cited

U.S. PATENT DOCUMENTS

| | | | |
|---|---|---|---|
| 6,513,532 B2 | 2/2003 | Mault et al. | |
| 6,837,827 B1 * | 1/2005 | Lee et al. | 482/8 |
| 7,063,644 B2 | 6/2006 | Albert et al. | |
| 7,647,196 B2 | 1/2010 | Kahn et al. | |
| 7,662,065 B1 * | 2/2010 | Kahn et al. | 482/9 |
| 2001/0049470 A1 | 12/2001 | Mault et al. | |
| 2003/0065257 A1 | 4/2003 | Mault et al. | |
| 2004/0229729 A1 | 11/2004 | Albert et al. | |
| 2005/0159272 A1 | 7/2005 | Chen | |
| 2005/0172975 A1 | 8/2005 | Downs | |
| 2005/0240086 A1 | 10/2005 | Akay | |
| 2005/0245793 A1 | 11/2005 | Hilton et al. | |
| 2005/0272564 A1 * | 12/2005 | Pyles et al. | 482/54 |
| 2005/0283051 A1 * | 12/2005 | Chen | 600/300 |
| 2006/0217231 A1 * | 9/2006 | Parks et al. | 482/3 |
| 2007/0135264 A1 | 6/2007 | Rosenberg | |
| 2007/0287596 A1 * | 12/2007 | Case et al. | 482/8 |
| 2008/0200310 A1 * | 8/2008 | Tagliabue | 482/8 |
| 2009/0043531 A1 | 2/2009 | Kahn et al. | |

FOREIGN PATENT DOCUMENTS

| | | |
|---|---|---|
| KR | 20020013214 A | 2/2002 |
| WO | 0152718 A2 | 7/2001 |
| WO | 0247465 A2 | 6/2002 |
| WO | 2009021147 A1 | 2/2009 |

* cited by examiner

*Primary Examiner* — Loan Thanh
*Assistant Examiner* — Shila Jalalzadeh Abyane
(74) *Attorney, Agent, or Firm* — Pearne & Gordon LLP

(57) ABSTRACT

A device for analyzing and monitoring exercise done by a user comprises at least a portable support (2), electric power supply means, sensor means (3) for measuring the exercise done by the user during at least one predetermined period of time, expressed at least in the form of at least one non-dimensional parameter, at least one memory (4) designed to archive data relating to the measurement of exercise done by the user, display means (5) for displaying the measurement of the exercise done by the user and the data archived in the memory, data communication means (6*a*), (6*b*) and at least one processing unit (7*a*), (7*b*).

19 Claims, 2 Drawing Sheets

DEVICE FOR ANALYZING AND MONITORING EXERCISE DONE BY A USER

BACKGROUND OF THE INVENTION

The present invention relates to a device for analyzing and monitoring exercise done by a user.

In the fitness sector for some time now there have been various widely used prior art devices for monitoring exercise done by a user while working out or, more generally, throughout the entire day, to provide the user with information regarding the amount of exercise done: in this way, the user can deduce whether or not said amount is sufficient to satisfy his training, weight loss or other program, or whether he must increase it, and by how much.

Obviously, such devices are typically portable, that is to say, pocket size, or equipped with special "clips" for fixing them to clothing. This makes them suitable for measuring exercise done by the user anywhere and at any time of day.

Some of these devices are generally called pedometers, and have a mechanism (springs, accelerometer and other parts) designed to calculate the number of steps taken by the user during the period of time for which he carries it with him, having means for displaying said number.

As already indicated, said devices are specially designed and made to calculate simply the number of steps taken by the user, without being able to measure in any way the intensity and speed with which said steps were taken. For example, with a conventional pedometer it is not possible to tell whether the steps were taken while walking or running. The difference between the two types of exercise is, obviously, significant.

Some models of pedometers based on accelerometers can measure the speed of the step and roughly determine the intensity of the movement. Other, more complex but still portable devices have not just an accelerometer, but also a processor which, using a suitable algorithm, allows the calculation, after entry of "input" data such as the user's gender, age, height, weight, of the amount of calories burned by the user during a predetermined period of time (typically the entire day) based on the measurements taken with the accelerometer, so as to provide indications regarding the amount of exercise done, which may be referred to the training program.

There are also known exercise machines (treadmills, exercise bicycles) equipped with at least one processor able to calculate, based on parameters recorded during machine operation, the amount of exercise done. Said exercise machines are specially equipped with a display for displaying said amount of exercise, for example in terms of time, distance covered, intensity, calories burned (obviously, provided the user entered his identification parameters, that is to say, gender, age, height, weight, etc.).

Nowadays in the fitness sector the need is felt to be able to provide the user, or his trainer, with complete information about the overall exercise done during a predetermined period of time (for example an entire day), both on machines (treadmills, exercise bicycles, etc.) and, for example, outdoors by walking or running or playing a sport, so as to be able to analyze the cumulative exercise in the most precise and accurate way possible.

However, it has been found that the use of devices such as conventional pocket size pedometers or the like on exercise machines (typically treadmills) generates rather significant measuring errors, which therefore do not allow the user and/or his trainer to evaluate with sufficient precision the overall amount of exercise done. In other words, it is not possible to obtain a precise and accurate evaluation of the sum of exercise done on exercise machines and that done outdoors (walking, running or playing a sport).

Therefore, in the sector, in response to this important demand, exercise machines (in particular treadmills) were created which are specifically set up to interact with portable measuring devices such as pedometers, using known means of communication. One example of this appears in United States patent application No. US2005/0272564. Said patent application describes a treadmill designed to receive information transmitted by a pedometer so as to record, in a suitable treadmill memory, the measurements taken by the pedometer in a predetermined period of time, and also able to display said measurements on the machine display so as to make them known to the user and/or the trainer.

An evident disadvantage of such a piece of equipment is the fact that the processors of modern exercise machine, together with the various measuring sensors they control, are typically and now generally designed to calculate and display information relating to user exercise mainly in terms of distance covered and/or calories burned, therefore they are not well suited to data consisting of the number of steps taken. As may be inferred from the above-mentioned patent application, the latter data is essential particularly in order to carry out those specific and well known training programs based on "10000 steps a day", but not for programs for training and/or maintaining weight designed according to calories consumed or overall exercise done during a day. Moreover, measuring steps is not suitable for measuring and adding together the exercise done on exercise machines which have a movement different to walking or running, for example exercise bicycles, rowing machines, machines with elliptical movement and others.

Another major disadvantage of both portable devices for measuring exercise (pedometers or the like) and exercise machines relates to the fact that all training programs set up on them which set goals (known in the sector as "goal training"), are set up based on considerations which are so generic and impersonal (for example the above-mentioned "10000 steps a day") that they rarely meet the actual needs of each user and equally rarely adapt to the actual physical conditions of the user.

SUMMARY OF THE INVENTION

The main technical purpose of the present invention is to overcome the above-mentioned disadvantages by providing a device for analyzing and monitoring exercise done by a user that can precisely and accurately record the overall exercise done by the user both outdoors (for example walking, running or playing any sport) and in the gym on one or more types of exercise machines.

Within the scope of said technical purpose, the present invention has for an aim to provide a device for analyzing and monitoring exercise done by a user designed to produce goal training programs which can be adapted to the actual needs and physical conditions of each user, day by day. In particular, setting a personal and realistic "goal" based on the exercise values recorded in the past by the user.

Another aim of the present invention is to provide a device for analyzing and monitoring exercise done by a user designed to generate goal training programs which are highly customized, that is to say, set according to the personal physical and psychological features of the user, and not generic programs used indiscriminately for large numbers of users.

Another aim of the present invention is to devise a device for analyzing and monitoring exercise done by a user which allows the user to be strongly motivated to do the greatest amount of exercise possible during the day.

Yet another aim of the present invention is to provide a device for analyzing and monitoring exercise done by a user designed to interact and exchange information with other devices of various types, such as exercise machines, personal computers, palmtops, mobile phones, computer networks, databases and the like.

Another aim of the present invention is to provide a device for analyzing and monitoring exercise done by a user which has a simple structure, is easy to make in practice, operates safely and effectively and is relatively inexpensive.

BRIEF DESCRIPTION OF THE DRAWINGS

The technical characteristics of the invention, with reference to the above aims, are clearly described in the claims below, and its advantages are more apparent from the detailed description which follows, with reference to the accompanying drawings which illustrate a preferred embodiment of the invention provided merely by way of example without restricting the scope of the inventive concept, and in which:

DESCRIPTION OF THE PREFERRED EMBODIMENTS

Figure 1:
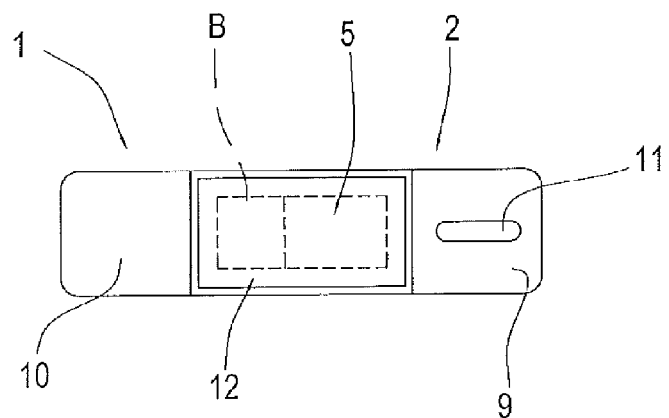
FIG. 1 is a front view of the device in accordance with the invention.

With reference to the accompanying drawings, and in particular with reference to FIG. 1, the numeral 1 denotes as a whole a device for analyzing and monitoring exercise done by a user made in accordance with the invention, in a first example embodiment.

Advantageously, the device comprises at least one portable support, labeled 2 as a whole in FIG. 1, having dimensions suitable for insertion, for example, in a pocket in clothing or, even more conveniently, allowing it to be fixed to the outside of clothing, so that it is immediately visible (described in more detail below).

Figure 6:
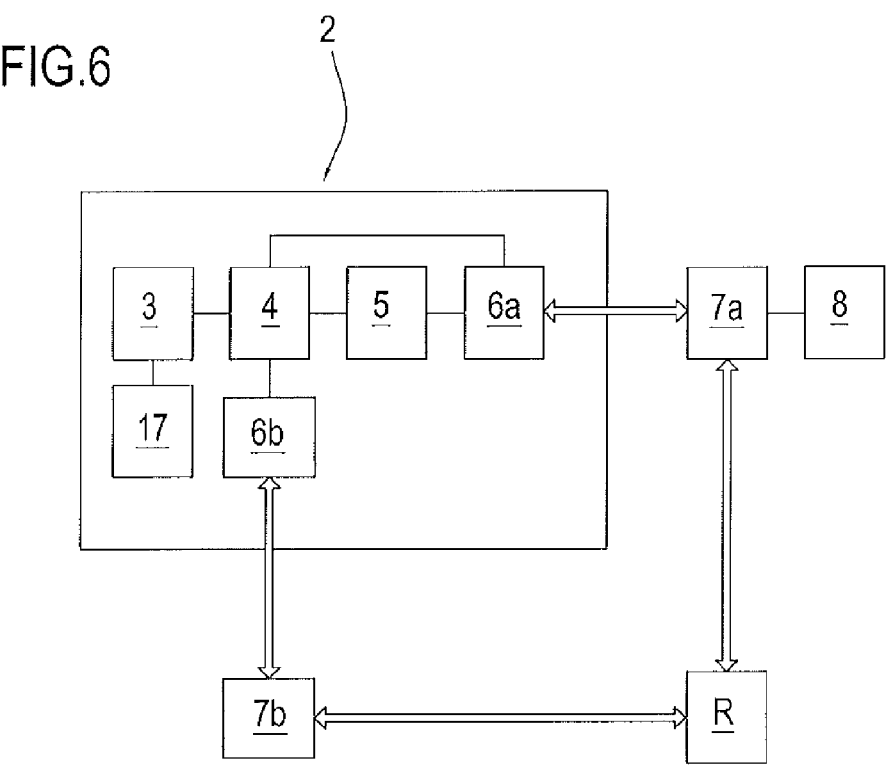
FIG. 6 is a circuit diagram of the device in accordance with the invention.

With reference to FIG. 6, which shows a device circuit diagram, it may be seen that the device also comprises sensor means, labeled 3, for measuring exercise done by the user wearing the portable support 2, according to methods and criteria described in detail below.

There is also at least one memory, labeled 4, designed to archive data relating to the exercise done by the user, and if necessary even data relating to the user himself (in particular, relating to his physical condition).

To allow the device user to read the data relating to the measurement of his exercise when he wants to, display means 5 are suitably provided for displaying the above-mentioned measurement and all of the data saved in the memory 4.

Finally, the device comprises suitable data communication means, labeled 6a, 6b in FIG. 6, which allow information about exercise done by the user, that is to say, basically the data measured by the sensor 3, to be transferred to at least one processing unit 7a, 7b of the substantially known type. In more detail, but by way of example only, the processing unit 7a, 7b could be of the type connected to at least one piece of exercise equipment, labeled 8 in FIG. 6, for performing aerobic exercises (such as exercise bicycles, treadmills and the like) or non-aerobic exercises, or it could even be a personal computer, a palmtop, or other similar processing devices. In the following description several example embodiments are referred to which will allow a clear indication of the advantages of the various possible solutions.

The sensor means 3 of the device disclosed comprise at least an accelerometer, for example of the piezoelectric type, having characteristics which are basically known and preferably connected to respective means for processing and treating the signals generated by it. Said processing and treatment means are of the known and conventional type and are indicated in FIG. 6 with the reference number 17.

As is known, the signal generated by the accelerometric sensor 3, if suitably treated and processed, is substantially directly proportional to the exercise done by the user wearing the device. The acceleration value measured, according to a predetermined sampling frequency, constitutes an optimum estimate of the amount of exercise (whether it is walking, running, or another form of exercise) that the user has done in a predetermined period or "window" of time in which his movements are measured (that is to say, the time during which he carried the device with him).

The device memory 4 is also of the substantially conventional type, and has a capacity and characteristics such that it satisfies the application requirements of the device disclosed.

The data communication means suitably comprise at least an RFID (Radio Frequency Identification) type aerial, labeled 6a in FIG. 6, designed to interact with at least one RFID type reader. Said RFID reader is not illustrated in the above-mentioned Figure because it is basically of the conventional type. Preferably, but not exclusively, the RFID reader is operatively connected to the processing unit 7a connected to the exercise machine 8. More particularly, the processing unit 7a suitably consists of a processor of the type which nowadays manages and controls all of the functions of a modern exercise machine, whilst the RFID reader is typically installed on the console of the exercise machine 8. However, it should be noticed that the data communication means could be of another type, that is to say, made using a technology that is alternative and equivalent to RFID technology.

The RFID aerial 6a and the respective RFID reader advantageously allow data about the user wearing the device (that is to say, basically his identity) and the exercise he has done (that is to say, the measurement of said exercise) to be transferred from the memory of the exercise machine 8 (not illustrated in the Figures) to the device memory 4. Moreover, the RFID aerial 6a and the respective RFID reader allow data about the user wearing the device (his identity) and the exercise he has done (the measurement) to be transferred from the device memory 4 to the memory of the exercise machine 8. In addition, the RFID aerial 6a and the respective RFID reader allow a plurality of training programs predetermined by the user, or by his trainer, which will be performed on one or more exercise machines, to be transferred from the device memory 4 to the memory of the exercise machine 8, and vice versa.

The processing unit 7a connected to the exercise machine 8 can also be put into communication and dialogue with a remote processor R (at the gym or another site), or equivalently with a network of processors (at the gym or another site), so that the information about the exercise done on the exercise machine can be transferred, managed and archived in suitable databases which the user and/or trainer can consult. Said databases may be managed for example by the gym, or by other companies specializing in the supply of services to assist with training and exercising.

Advantageously, the data communication means also comprise at least one USB (Universal Serial Bus) type connector, labeled 6b in FIG. 6, basically of the conventional type, which allows connection to a processing unit 7b consisting for example of a personal computer, a palmtop or the like. In more detail, the processing unit 7b allows the data contained in the memory 4 to be displayed, and also allows the data to be processed according to the methods and criteria preferred by the user and/or his trainer. By way of example only, it should be noticed that the transfer of data from the memory 4 to the processing unit 7b (personal computer or the like) helpfully allows the user and/or his trainer to display the measurements in the form of graphs, to carry out studies, calculations and planning of training based on past measurements and many other activities of this type, using specially designed and made software.

Figure 5:
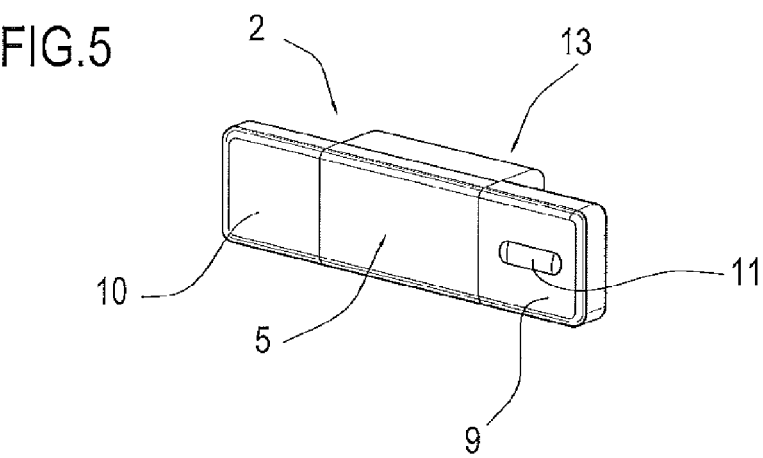
FIG. 5 is a perspective view of the device.

FIG. 5 is a perspective view of the portable device disclosed. As shown in FIG. 5, the device portable support 2 (for example made of a material such as plastic or the like) substantially has the shape of a parallelepiped, having a first projection 9 and a second projection 10, in opposite directions, extending from the two ends of the parallelepiped.

At the first projection 9 (on the right-hand side) there is the male USB connector 6b, with respective protective cover. Moreover, on the same first projection 9 there is a navigation button 11, operatively connected to the memory 4 and to the display means 5, which allows the user to display at least one screen page presenting information mainly about the measurement of the exercise done by the user and, at the user's discretion, other types of information which may be available (for example the date, time, or other information). The RFID aerial 6a is located at the second projection 10 (on the left-hand side). The second projection 10 is suitably sized to allow it to be inserted in a suitable slot in the console of the exercise machine 8, where the RFID reader is mounted, the latter being designed to interact with the RFID aerial 6a. Therefore, in this way, the data may be transferred from the device memory 4 to the memory of the exercise machine 8 and vice versa.

The display means 5 of the device in accordance with the invention suitably comprise at least one window, made at the centre of the front face 12 of the portable support 2, having suitable dimensions sufficient to allow the user to read the information without any difficulty. The information about the measurement of the exercise done by the user can be made available to the user in various ways, at his own discretion.

A first advantageous method of displaying the measurement of the exercise done by the user on the display means 5 consists of a graphic signal indicating the measurement of the exercise done by the user in terms of quantity. In more detail, said graphic signal indicating the measurement of the exercise done by the user consists of at least one horizontal bar, indicated with a dashed line and labeled B in FIG. 1, white or luminous, whose length is proportional to the exercise effectively done and recorded by the device. The maximum length of the bar, or in other words when it is completely filled, in practice corresponds to achievement of a predetermined exercise goal, as described in more detail below. This method of displaying the measurement of the exercise done by the user is particularly advantageous, since it is immediate and intuitive, without being linked to any numeric data.

A second advantageous method of displaying the measurement of the exercise done by the user on the display means 5 consists of displaying at least one non-dimensional numeric parameter, indicating the measurement of the exercise done by the user. Said numeric parameter, which is substantially directly proportional to the accelerometric measurements of the sensor 3, does not depend on any information relating to the physical condition of the user (typically age, gender, height, weight, etc.), and its order of magnitude (units, tens, hundreds) can be suitably selected at the design step to meet user requirements in the best possible way, so as to better motivate users to exercise as much as possible. In fact, it has been empirically proven that numeric parameters expressed in units and decimals rather than in tens or hundreds have a different psychological impact on user motivation. To further motivate the user to exercise, preferably both the current numeric parameter and the goal to be reached, also expressed in the form of a numeric parameter, may be displayed together.

A third method of displaying the measurement of the exercise done by the user on the display means 5 consists of displaying the current value and goal value for calories burned, if the data item relating to the basal metabolism (known as the BMR, Basal Metabolic Rate) has been entered in the device somehow.

A fourth method of displaying the measurement of the exercise done by the user on the display means 5 consists of displaying the current value and goal value for distance covered.

A fifth method of displaying the measurement of the exercise done by the user on the display means 5 consists of displaying the current value and goal value for the period of time spent exercising.

A sixth method of displaying the measurement of the exercise done by the user on the display means 5 consists of displaying the current value and goal value for steps taken.

Figure 2:
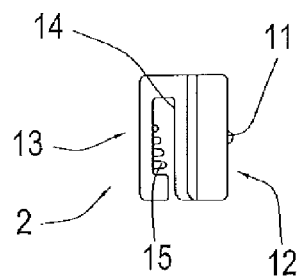
FIG. 2 is a side elevation view of the device of FIG. 1.

The portable support 2 advantageously comprises means which allow the device to be removably fixed to the user's clothing, said means labeled 13 in FIG. 2. The user can use said removable fixing means to always carry the device disclosed with him, recording any type of exercise done and also being able to read the information displayed on the display means 5 at any time. The removable fixing means preferably consist of an elastically flexible tab 13, integral with the rear face 14 of the portable support 2, which allows the device to be fixed for example to the waistband of a pair of pants, or to the edge of a pocket, or in other convenient positions. Advantageously, there are stiffening ribs 15 along the inner face of the tab 13.

Figure 3:
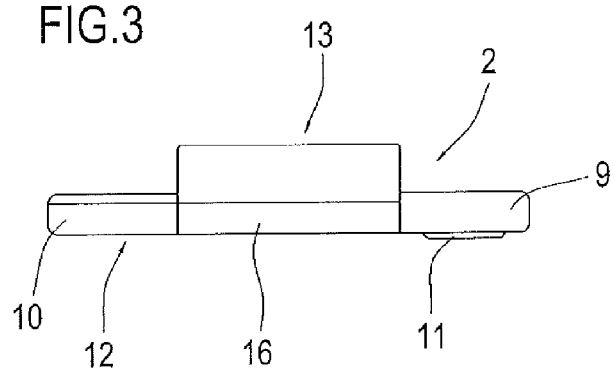
FIG. 3 is a top view of the device.
Figure 4:
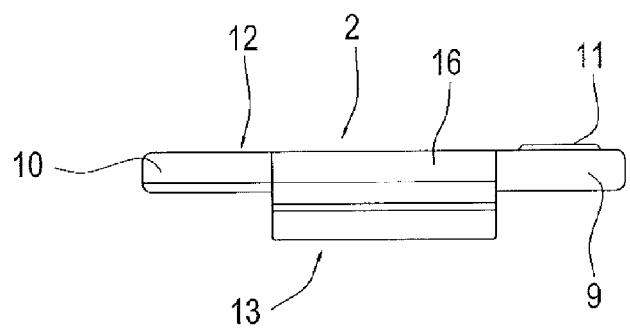
FIG. 4 is a bottom view of the device in accordance with the invention.

Finally, obviously, the device disclosed comprises electric power supply means, indicated with the reference number 16 in FIGS. 3 and 4, which are of the known and conventional type. The electric power supply means may consist, for example, of a disposable battery or a rechargeable battery.

The method for using the device disclosed is described below, by way of example, and without in any way limiting the scope of the invention.

As already indicated, the device is designed to exchange information, by means of the RFID aerial 6a and respective RFID readers, with all types of exercise machines typically present in a modern gym. This allows the user, first, to use the device to obtain an optimum guide and assistance in his training session in the gym.

In more detail, the device memory 4 is used to initially save user identification data, in particular relating to his biometric characteristics (personal details, height, weight, basal metabolism and any other useful information), through interaction with a suitable central processor located in the gym. In practice, that is done by inserting the second projection 10 of the device portable support 2 in a suitable slot in the central processor located in the gym, there being an RFID reader at said slot. On this occasion, or in other subsequent situations, at least one algorithm can be set in the device memory 4 to set the daily exercise goal which the user must reach, decided by the trainer together with the user according to his specific requirements (for example a specific program for weight loss, to improve cardiovascular conditions, or another program). Said algorithm may be designed according to different interpretations and strategies, described in more detail below.

Before starting each training session, the user inserts the second projection 10 of the device portable support 2 in the appropriate slot in the central processor located in the gym. In this way, all updated training programs relating to all of the exercise machines the user must use in the gym during that session are saved to the device memory 4. The above-mentioned training programs were previously prepared by the user's trainer, using suitable management software, mainly relating to the daily exercise goal to be reached. Obviously, such training programs are constantly updated by the trainer and/or by the management software so as to demand increasing and diversified effort from the user with the passage of time as regards the daily goals.

For each exercise machine that the user will have to use, he inserts the second projection 10 of the device portable support 2 in the suitable slot in the console of the exercise machine, there being an RFID reader at said slot. In this way, the training program for that specific exercise machine is transferred from the device memory 4 to the machine memory. Therefore, based on said program, the machine processor can adjust the machine typical operating parameters (duration, intensity) for the exercise to be done.

At the end of each training session on each machine, the processor transfers the data present in its memory to the device memory 4. Said data represents the exercise done by the user on the machine in question, and contributes to increase the cumulative measurement of the overall exercise done by the user that particular day. Obviously, this increase can be displayed at any time on the device display means 5 according to the method preferred by the user (bar which gets longer, non-dimensional numeric parameter, both, or another method).

When all of the training sessions have been completed on all of the machines programmed, the user again inserts the second projection 10 of the device portable support 2 in the appropriate slot in the central processor located in the gym, so that the management software can update the user history with the data relating to the exercise done on the machines. In this way, all of the information is made available for the user and the trainer to consult and study.

In turn, the management software is put into communication with at least one remote server, which can also be accessed via the internet, on which all updated information relating to the user resides.

The method for use described above relates exclusively to monitoring and management of exercise done in the gym on exercise machines.

Advantageously, as already indicated, the device disclosed also allows the recording and evaluation of exercise done outside the gym, before and after the "indoor" training session. By simply wearing the device (preferably using the removable fixing means 13), the sensor means 3 record, from one moment to the next, the exercise done by the user (walking, running, other sports) throughout the entire period of time during which the device is worn. At any time the user can use the display means 5 to display the measurement of the exercise done up to that moment (with one of the methods described above) compared with the daily goal to be reached, so as to greatly motivate the user.

The overall measurement of overall exercise done by the user, contained in the device memory 4, can then be transferred to the remote server which contains all information relating to the user. This is easily done by inserting the USB connector 6a in the USB port of a personal computer. Once the computer has recognized the device, a connection to the remote server via the internet is automatically established, through which the data contained in the device memory 4 is transferred to and saved on the server, so as to update the user history.

In addition, a user who has an exercise machine at home can, according to a method of use substantially similar to that described for the machines in the gym, and which is not repeated herein, save the data relating to training done on the home machine to the device memory 4. As described above, said data can then be transferred via the internet to the remote server, to update the user history with all exercise done, that is to say in the gym, outdoors and (if any) on a home exercise machine.

As already indicated, the daily exercise goal which each user must reach may be set according to different strategies, from the simplest to the most complex. Below are several method for setting the daily goal, examples which should be considered simply provided by way of example and not exclusive.

The first example of a method for setting the daily goal consists of implementing one after another the steps of measuring the exercise done by the user in a predetermined period of time preferably, but not exclusively, consisting of an entire day, cumulative saving (in the memory 4) of said exercise measurement, calculation of the arithmetic mean of a predetermined number of exercise measurements previously saved (preferably, but not exclusively, said predetermined number consists of a week, that is to say, seven daily measurements), and finally displaying on the display means 5 the request that the user exceeds said arithmetic mean by a predetermined amount within a further predetermined period of time (that is to say, a subsequent day). Therefore, in other words, the user is asked to exceed by a predetermined minimum amount the mean of the exercise measurements taken for the previous seven days. In the medium-term this causes an increase in the level of exercise.

The second example of a method for setting the daily goal consists of implementing one after another the steps of setting a long-term exercise goal, measuring the exercise done by the user in a predetermined period of time preferably, but not exclusively, consisting of an entire day, cumulative saving (in the memory 4) of said exercise measurement, calculation of the arithmetic mean of a predetermined number of exercise measurements previously saved (preferably, but not exclusively, said predetermined number consists of a week, that is to say, seven daily measurements), and finally displaying on the display means 5 the request that the user exceeds the lesser value out of said arithmetic mean and the long-term goal by a predetermined amount within a further predetermined period of time (that is to say, a subsequent day). Therefore, once said long-term goal has been reached the user is not automatically asked to increase his level of daily exercise. The long-term goal value can be set in advance based on typical values for generic categories of users, or it can be set by the user or his trainer.

The third example of a method for setting the daily goal consists of implementing one after another the steps of measuring the exercise done by the user in a predetermined period of time preferably, but not exclusively, consisting of an entire day, cumulative saving (in the memory 4) of said exercise measurement, and displaying on the display means 5 the request that within a further predetermined period of time (that is to say, another day) the user exceeds by a predetermined amount the exercise measurement saved in a predetermined period of time selected at the discretion of the user and/or the trainer. The latter predetermined period of time is preferably the same day of the previous week. If there are no measurements available from the previous week, a typical reference value for generic categories of users is set, or a value set by the user and/or the trainer. This method is definitely more effective at increasing exercise amongst users whose levels of exercise vary greatly during the week, and whose average level of exercise would not be very significant.

The fourth example of a method for setting the daily goal consists of implementing one after another the steps of setting a long-term exercise goal, measuring the exercise done by the user in a predetermined period of time preferably, but not exclusively, consisting of an entire day, cumulative saving (in the memory 4) of said exercise measurement, and displaying on the display means 5 the request that the user exceeds the lesser value out of the exercise measurement saved in a predetermined period of time selected at the discretion of the user and/or the trainer and the long-term goal by a predetermined amount within a further predetermined period of time (that is to say, another day). Said predetermined period of time is preferably the same day of the previous week, as described in the previous example.

The fifth example of a method for setting the daily goal consists of implementing one after another the steps of setting a minimum exercise goal, setting a higher increase for the goal, and setting a lower increase for the goal. This is followed by a step of comparing the exercise measurement relating to the predetermined immediately previous period of time (preferably the previous day) with the average of the exercise measurements in a predetermined number of previous predetermined periods of time (preferably the previous seven days). If the exercise measurement relating to the previous day is greater than the average of the exercise measurements in the previous week, there follows a step of assignment, to the average of the exercise measurements in the previous week, of the greatest value out of the average of the measurements for all of the previous days and the sum of the average of the exercise measurements in the previous week with the above-mentioned predetermined higher increase.

If, instead, the exercise measurement relating to the day immediately previous is less than the average of the exercise measurements relating to the previous week, there follows a step of assignment, to the average of the exercise measurements in the previous week, of the greatest value out of the sum of the average of the exercise measurements in the previous week with the predetermined lower increase, the average of the measurements for all of the previous days and the above-mentioned minimum goal.

Finally, there follows a step of assignment, to the current day's goal, of the difference between the average of the exercise measurements for the previous week multiplied by seven and the sum of the exercise measurements in a number of previous days equal to said predetermined number minus one unit, that is to say equal to six.

The latter method is particularly effective for discouraging the user from reducing his exercise. The two increases, higher and lower (preferably expressed as percentages) basically determine the speed with which the average reference value for the week varies. For example, the lower increase parameter (expressed as a percentage) gradually reduces the weekly average goal relative to the value reached during the previous day. Should a user suddenly stop exercising in the gym, the effect of this decision on the calculation of average exercise would be significant, resulting in very high daily goals being set for the user to compensate for stopping exercising in the gym and to remain at average levels. To avoid this, instead of recalculating the average exercise, the method described above reduces the average by a predetermined number of percentage points (lower increase).

The sixth example of a method for setting the daily goal uses the data of the measurements of the last two weeks and consists of calculating a daily "gap" for the last seven days, defined as the difference between the measurement for the day and the value measured the previous week (the "day gap").

In particular, this method consists of cumulating the values of the day gaps for the previous seven days. If said cumulated value is negative or null, there is no gap to recover, and the value measured the previous week is assigned. If instead the cumulative value is positive, it means that there is an exercise gap to be recovered, therefore a daily goal equal to one seventh of the cumulated gap added to the value measured the previous week is assigned.

If a daily goal is assigned which exceeds the value measured the previous week by more than a predetermined value (for example 50%), then the daily goal is limited to 150% of the value for the previous week.

This example embodiment is particularly advantageous because it is known that the exercise routine followed by users may not be rigid or, even if regular, may show exceptions to said regularity. By calculating the average of the values for the same day from two weeks, the same value is always set for regular users. For non-regular users or those for whom exceptions apply, the daily goal set is an intermediate "preliminary" value, since the device cannot know the effective future behavior of the user.

The invention described above is susceptible of industrial application and may be modified and adapted in several ways without thereby departing from the scope of the inventive concept. Moreover, all details of the invention may be substituted by technically equivalent elements.

What is claimed is:

1. A device for analyzing and monitoring exercise done by a user, comprising a portable support whereby the device can be worn by the user, wherein the device further comprises electric power supply means, sensor means, for measuring the exercise done by the user during at least one pre-determined period of time during which the device is worn, expressed in the form of a non-dimensional numeric parameter, at least one memory designed to archive data relating to the measurement of exercise done by the user, display means for displaying said non-dimensional numeric parameter in comparison with a pre-determined exercise goal and the data archived in the memory, data communication means for connection to at least one external processing unit, wherein the sensor means comprises at least one accelerometer, connected to a respective means for processing and treating signals which it generates, for calculating said non-dimensional numeric parameter, wherein said pre-determined exercise goal is set on a daily or long-term basis and is representative of a cumulative amount of physical exercise that the user aims at achieving on a temporal basis, said display means being configured to display in real time an actual amount of exercise carried out by the user on said temporal basis, resulting from a cumulative measurement of the exercise carried out by the user, in comparison with the pre-determined exercise goal, wherein said display means is further configured to display at least one graphic signal indicating the measurement of exercise done by the user in relation to said pre-determined exercise goal, said graphic signal consisting of a single bar whose filled length is proportional to the amount of exercise done on said temporal basis, whereby the bar is completely filled when the pre-determined exercise goal is reached, wherein the portable support has an elongated geometry and has a first end and a second, opposite, end which define the elongated geometry, the device having a central portion, said central portion having a central portion width, the device having a first projection extending from the central portion along a longitudinal axis of the device in a first direction, said first projection having a first projection width and defining the first end, the device having a second projection extending from the central portion along the longitudinal axis of the device in a second direction, said second projection having a second projection width and defining the second end, the first direction being opposite the second direction, wherein the first projection width is equal to the central portion width and the central portion width is equal to the second projection width, and wherein at least one of said first and second projections defines a connector, said connector providing said data communication means.

2. The device according to claim 1, wherein the data communication means comprise at least one RFID (Radio Frequency Identification) type aerial designed to interact with at least one RFID type reader operatively connected to the at least one external processing unit, connected to at least one exercise machine.

3. The device according to claim 2, wherein the RFID aerial and reader are designed to transfer data about the user and exercise done by the user from a memory of the exercise machine to the at least one memory of the device.

4. The device according to claim 2, wherein the RFID aerial and reader are designed to transfer data about the user and exercise done by the user from the at least one memory of the device to a memory of the exercise machine.

5. The device according to claim 2, wherein the RFID aerial and reader are designed to transfer at least one pre-determined user training program data from the at least one memory of the device to a memory of the exercise machine.

6. The device according to claim 1, wherein the data communication means comprise at least one USB (Universal Serial Bus) connector for connecting to at least one external processing unit connected to a personal computer designed to display the data contained in the at least one memory of the device and designed to process the data according to methods pre-determined by the user and/or by his trainer.

7. The device according to claim 6, wherein the personal computer is designed to connect to at least one remote server having at least one database for saving the measurements of exercise done by the user.

8. The device according to claim 1, wherein said accelerometer is of the piezoelectric type.

9. The device according to claim 1, wherein the at least one external processing unit consists of at least one personal computer.

10. The device according to claim 1, wherein the data communication means comprise at least one RFID (Radio Frequency Identification) type aerial designed to interact with at least one RFID type reader operatively connected to the at least one external processing unit.

11. The device according to claim 1, wherein the data communication means comprise at least one USB (Universal Serial Bus) connector for connecting to at least one external processing unit designed to process the data contained in at least one memory of the device according to methods pre-determined by the user and/or by his trainer.

12. The device according to claim 1, wherein the data communication means comprise at least one USB (Universal Serial Bus) connector for connecting to the at least one external processing unit connected to an exercise machine designed to display the data contained in the at least one memory of the device and designed to process the data according to methods pre-determined by the user and/or by his trainer.

13. The device according to claim 1, wherein the portable support comprises at least one button, operatively connected to the at least one memory of the device and to the display means, the display means being designed to display at least one screen page presenting information relating to the measurement of exercise done by the user on the display means.

14. The device according to claim 1, wherein the portable support comprises means for removably fixing the device to a user's clothing.

15. The device according to claim 1, wherein the at least one external processing unit is designed to be put into communication with at least one remote processor for managing and archiving data relating to exercise done by the user.

16. The device according to claim 1, wherein the data communication means is connectable to an exercise equipment for retrieving and storing into the at least one memory of the device data related to the exercise done by the user on the exercise equipment, said non-dimensional numeric parameter being calculated based on the data stored in the at least one memory of the device, collected from the sensor means and retrieved from said exercise equipment.

17. The device according to claim 1, wherein the device is configured to allow a transfer of data from an exercise machine to the at least one memory of the device through said data communication means, when the device is coupled to the exercise machine, at the end of a training session, and wherein the processing means of the portable device are configured to analyze said data, whereby said data contribute to increase the cumulative measurement of the overall exercise done by the user.

18. The device according to claim 1, wherein said connector is a USB connector.

19. The device according to claim 1, wherein each one of the two projections defines a respective connector.

* * * * *